(12) United States Patent
Chen et al.

(10) Patent No.: US 11,365,423 B2
(45) Date of Patent: *Jun. 21, 2022

(54) **METHOD OF OBTAINING MULTILEAFLET *MEDICAGO SATIVA* MATERIALS BY MEANS OF *MSPALM1* ARTIFICIAL SITE-DIRECTED MUTANTS**

(71) Applicant: Guangdong Sanjie Forage Biotechnology Co., Ltd, Guangzhou (CN)

(72) Inventors: Haitao Chen, Guangzhou (CN); Wen Wang, Guangzhou (CN); Xiongping Xie, Guangzhou (CN); Qiang Qiu, Guangzhou (CN); Zhanhuan Shang, Guangzhou (CN); Kexian Su, Guangzhou (CN); Hui He, Guangzhou (CN)

(73) Assignee: GUANGDONG SANJIE FORAGE BIOTECHNOLOGY CO., LTD, Guangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 17/141,308

(22) Filed: Jan. 5, 2021

(65) Prior Publication Data

US 2021/0171973 A1    Jun. 10, 2021

Related U.S. Application Data

(63) Continuation of application No. 17/257,595, filed as application No. PCT/CN2019/094632 on Jul. 3, 2019.

(30) Foreign Application Priority Data

Jul. 4, 2018    (CN) .......................... 201810724563.3

(51) Int. Cl.
    *C12N 15/82*    (2006.01)
(52) U.S. Cl.
    CPC ..... *C12N 15/8262* (2013.01); *C12N 15/8213* (2013.01)
(58) Field of Classification Search
    None
    See application file for complete search history.

(56) References Cited

U.S. PATENT DOCUMENTS

| 2011/0289625 A1* | 11/2011 | Chen | C12N 15/8247 |
|---|---|---|---|
| | | | 800/279 |
| 2016/0264982 A1* | 9/2016 | Zhu | C12N 15/8213 |

FOREIGN PATENT DOCUMENTS

| CN | 104737899 A | 7/2015 |
|---|---|---|
| CN | 108949774 A | 12/2018 |

OTHER PUBLICATIONS

Zhang et al 2010 (Agricultural Sciences in China 9:2, p. 170-178) (Year: 2010).*

Xiaolong, Wang et. al. "Research progress of multi-leaf alfalfa" Heilongjiang Animal Husbandry and Veterinary Medicine, 515, Dec. 10, 2016, DOI-10.13881/j.cnki.hljxmsy.2016.2285.

Juan, N.A., Sheaffer, C.C., Barnes, D.K., Swanson, D.R. and Halgerson, J.H. (1993), Leaf and Stem Traits and Herbage Quality of Multifoliolate Alfalfa. Agron. J., 85: 1121-1127. https://doi.org/10.2134/agronj1993.00021962008500060005x.

* cited by examiner

*Primary Examiner* — Matthew R Keogh
(74) *Attorney, Agent, or Firm* — IP Attorneys Group, LLC

(57) ABSTRACT

Disclosed is a method for obtaining multileaflet *Medicago sativa* materials by means of MsPALM1 artificial site-directed mutants. The method comprises: selecting a target site from an exon region of a compound leaf developmental regulatory gene MsPALM1 of *Medicago sativa* and constructing a plant CRISPR/Cas9 editing recombinant vector MsCRISPR/Cas9::PALM1 and introducing the vector into *Medicago sativa* cells and regenerating into plants, cutting and repairing to cause a loss-of-function mutation in the MsPALM1 gene of *Medicago sativa* cells, and then screening the mutant plants by restriction endonuclease digestion and/or targeted deep sequencing of the target sites of the regenerated plants to obtain lines carrying four MsPALM1 allelic genes with simultaneous loss of function mutation. After phenotypic identification, it was confirmed that the compound leaves of the regenerated plants changed from three leaflets to five leaflets. The method can quickly obtain multileaflet *Medicago sativa* materials with a short breeding period and stable trait.

6 Claims, 2 Drawing Sheets

Specification includes a Sequence Listing.

5'······ATGTTCACCGCCG CGACCGTGCTCGTCTCCATC······3'  WT
5'······ATGTTCACCGCCG CGA- CGTGCTCGTCTCCATC······3'  -1
5'······ATGTCCACCGCCG ---- CGTGCTCGTCTCCATC······3'  -4
5'······ATGTTCACCGCCG -GACCGTGCTCGTCTCCATC······3'  -1
5'······ATGTTCACCGCCGGCGACCGTGCTCGTCTCCATC······3'  +1
5'······CCGG----------------------------------TC······3'  -60
5'······ATGTTCACCGCCG C-----T-C--  GTCTCCATC······3'  -11/+2

METHOD OF OBTAINING MULTILEAFLET *MEDICAGO SATIVA* MATERIALS BY MEANS OF *MSPALM1* ARTIFICIAL SITE-DIRECTED MUTANTS

TECHNICAL FIELD

The present disclosure belongs to the technical field of biological breeding of *Medicago sativa*, and specifically pertains to a method of obtaining multileaflet *Medicago sativa* materials by means of MsPALM1 artificial site-directed mutants.

BACKGROUND

Alfalfa (*Medicago sativa* L.) is perennial high-quality legume forage with a long history of cultivation, with the characteristics of strong adaptability, high nutritional value, wide planting area, complete ecological functions and high economic benefits. As a perennial legume forage crop, it has the largest planting area in the world and is reputed as the king of forage. *Medicago sativa* has been cultivated for more than two thousand years in China. At present, the land area for planting *Medicago sativa* in China is over about 1.467 million hectares. The current level of production: the average hay yield is 13-17 t/hm$^2$, and the average seed yield is 375-600 kg/hm$^2$. Therefore, the grass industry in China is mainly the industrialization of *Medicago sativa*, which has a very important value and status in the development of agriculture and animal husbandry. It is of great significance to cultivate the varieties with high grass yield and protein content to promote the high-quality forage production and the development of animal husbandry in China.

The protein content of *Medicago sativa* is mainly concentrated in leaves, and the trait of leaves is related to the trait of yield. The leaves of *Medicago sativa* are generally ternate compound leaves. The detection data shows that, 60-70% of crude protein and 90% of vitamin are found in leaves of *Medicago sativa*, so high-quality *Medicago sativa* should be leafy. It is therefore determined that our breeding target is cultivating novel varieties with multileaflet, that is, to generate multileaflet *Medicago sativa* varieties with more than 3 leaflets per compound leave through mutation. The multileaflet trait of *Medicago sativa* is considered to have the potential for high yield and good quality. It is very important to cultivate high-quality *Medicago sativa* with multileaflet trait for the development and utilization of high-quality *Medicago sativa*. The multileaflet trait of *Medicago sativa* is also found in nature. Results of previous researches have shown that compared with trifoliolate *Medicago sativa*, the photosynthetic efficiency, the specific leaf weight, the stem-leaf ratio and other growth characteristics of multileaflet *Medicago sativa* are significantly enhanced; additionally, the multileaflet trait of *Medicago sativa* can increase the leaf area of *Medicago sativa*, which is positively correlated with the grass yield of *Medicago sativa*; the grass yield of multileaflet *Medicago sativa* lines is significantly higher than those of trifoliolate *Medicago sativa* varieties; however, the multileaflet trait of *Medicago sativa* are unstable and there is a recessive character of the multileaflet trait of *Medicago sativa*.

Although multileaflet material lines have broad application prospects in the cultivation of new high-quality *Medicago sativa* varieties, there are limited natural genetic mutation resources, and *Medicago sativa* is an autotetraploid plant that is cross-pollinated and has the characteristic of self-incompatibility. Therefore, it is not feasible to obtain a novel homozygous genetically stable *Medicago sativa* variety by traditional hybridization techniques, which has a long breeding period. It is known through searching that Patent No. CN104737899B—A method of breeding multileaflet *Medicago sativa* by space mutagenesis had bred the first new multileaflet *Medicago sativa* variety by space mutagenesis, but this method had the disadvantages of high cost, strict condition requirements, multi-generation hybrid breeding, repeated screening, instability, long time consuming and low repeatability.

In the study of *Medicago truncatula*, a proximal species of *Medicago sativa*, we found that the major gene that regulates the development of leaf primordium is PALM1 gene which is a single-copy gene with a single exon, and the recessive homozygous mutant of this gene has pentatrinate compound leaves. Using an efficient site-directed genome editing technology to silence four alleles of MsPALM1 of *Medicago sativa* simultaneously may rapidly generate a new genetically stable *Medicago sativa* variety with multileaflet trait. Therefore, we hope to obtain a method of obtaining multileaflet *Medicago sativa* materials by means of artificial site-directed mutants of a *Medicago sativa* compound leaf developmental regulatory gene MsPALM1, by which the four alleles of MsPALM1 of *Medicago sativa* can be silenced simultaneously and rapid orientation can be achieved to obtain multileaflet *Medicago sativa* materials.

SUMMARY

With respect to the above problems, the present disclosure provides a method of obtaining multileaflet *Medicago sativa* materials by means of MsPALM1 artificial site-directed mutants, the method comprises the following steps:

Step (1), Selecting a target site in an exon region of a compound leaf developmental regulatory gene MsPALM1 of *Medicago sativa*; wherein, one strand in the double-stranded structure of the target site has a structure of NGG, wherein N represents any one of bases A, T, C, G;

Step (2), According to the nucleotide sequence of the target site, constructing a binary expression vector MsCRISPR/Cas9::PALM1 which is used for transforming *Medicago sativa* by *Agrobacterium tumefaciens* and further editing the MsPALM1 gene of *Medicago sativa*; the MsCRISPR/Cas9::PALM1 vector comprises an sgRNA expression frame and a Cas9 gene expression frame, the sgRNA expression frame comprises the guide sequence of the target site;

Step (3), Introducing the binary expression vector MsCRISPR/Cas9::PALM1 into *Medicago sativa* cells, so that the sgRNA expression frame and the Cas9 nuclease expression frame are co-expressed in *Medicago sativa* cells; cutting the target site in the double-strand of MsPALM1 gene, inducing the DNA repairing function of *Medicago sativa* cells themselves; randomly inserting or deleting bases at target sites, resulting in frameshift mutations, so as to cause a loss-of-function mutation in the MsPALM1 gene of cells;

Step (4), Regenerating plants from the *Medicago sativa* cells in step 3;

Step (5), Performing PCR amplification on the DNA segment comprising the target site of MsPALM1 gene in the regenerated plants obtained from step 4, and then detecting by restriction endonuclease digestion and/or targeted deep sequencing;

Step (6), Selecting the regenerated plants carrying four alleles with simultaneous loss-of-function mutation for phenotypic identification, observing the compound leaf phenotype of the regenerated plants, and selecting plants with more than 3 leaflets in all the compound leaves as the generated multileaflet *Medicago sativa* material.

Preferably, one strand in the double-stranded structure of the target site has a structure of 5'-G(N)x-NGG-3', wherein, (N)x represents a sequence of x bases {N1, N2 . . . Nx}, and each of N1, N2 . . . Nx represents any one of A, G, C, T. X is generally 18 or 19.

Preferably, the sgRNA expression frame can be expressed in *Medicago sativa* cells and its nucleotide sequence is as shown in Seq ID NO. 1; the Cas9 gene expression frame can be expressed in *Medicago sativa* cells and its nucleotide sequence is as shown in Seq ID NO. 2. That is, on the other hand, the present disclosure also provides such a recombinant vector.

Preferably, the sgRNA expression frame comprises: a MtU6 promoter from *Medicago truncatula*, its nucleotide sequence is as shown in positions 1 to 500 of Seq ID NO. 1; a guide sequence of the target with a structural feature of G(N)x and an artificially synthesized sgRNA skeleton sequence, their nucleotide sequences are as shown in positions 501 to 606 of Seq ID NO. 1; and a Poly-T terminator, its nucleotide sequence is as shown in positions 607 to 615 of Seq ID NO. 1, The Cas9 gene expression frame comprises: a CaMV 35S promoter, its nucleotide sequence is as shown in positions 1 to 345 of Seq ID NO. 2; a Cas9 coding sequence, as shown in positions 487 to 4756 of Seq ID NO. 2; and a tNOS terminator, as shown in positions 4794 to 5046 of Seq ID NO. 2.

Preferably, the sgRNA expression frame comprises a CRISPR RNA sequence, which has G(N)x in 5'-G(N)x-NGG-3' of the target site or a complementary sequence thereof.

Preferably, the G(N)x in 5'-G(N)x-NGG-3' of the target site or the complementary sequence thereof comprises a sequence of 5'-GGAGACGAGCACGGTCGCGG-3' (Seq ID NO. 3), which is a reverse complementary sequence of the nucleotide sequence 5'-CCGCGACCGTGCTCGTCTCC-3' (Seq ID NO. 4) at the positions 323-343 after the translation initiation codon ATG in the single exon of MsPALM1 gene.

On the selected exon of MsPALM1 gene, there are totally 19 fragments with the structure of 5'-G(N)x-NGG-3' which can be selected as the target sites.

The loss-of-function mutation mentioned in step 6 means the occurrence of terminators or reading frame shifts at the target sites of normal MsPALM1 coding sequences.

The Cas9 nuclease expression frame is located in the same vector comprising the sgRNA expression frame.

In step 3, the obtained recombinant vector is introduced into *Medicago sativa* cells, so that the cells contain sgRNA of the target site and Cas9 nuclease in step 2 simultaneously. Under the combined action of sgRNA and Cas9 nuclease, the double-stranded target site of MsPALM1 gene is cut, additionally in combination with the DNA repairing function of the *Medicago sativa* cells themselves, random insertion and/or random deletion of MsPALM1 gene target site can be realized finally in the cells.

In the method, the recombinant vector is introduced into *Medicago sativa* cells by the stable transformation of *Medicago sativa* callus by *Agrobacterium*. During introducing the obtained recombinant vector into the *Medicago sativa* cells, the recombinant vector is introduced into the genomic DNA of *Medicago sativa* by an *Agrobacterium*-mediated method, so the target site of *Medicago sativa* is cut when transgenes are expressed.

In the present disclosure, the method of regenerating plants is to obtain plants through tissue culture of cells or tissues.

In step 5, the DNA fragments comprising the target site of MsPALM1 gene in the regenerated plants can be cloned by a PCR method with the genome DNA as template, and restriction endonuclease digestion and/or targeted deep sequencing are performed on the amplified products. The PCR method with the genome DNA as template is as below: against the genome region comprising the target site, designing site-specific primers; with the genome DNA of the regenerated plants as the template, amplifying the genome region comprising the target site. The restriction endonuclease digestion on the amplification products means that separating the amplification products by means of agarose gel electrophoresis, then recovering the DNA fragments comprising the target site, digesting the recovered DNA fragments comprising the target site with restriction endonuclease, and performing the agarose gel electrophoresis again; the resulting bands that cannot be digested with restriction endonuclease are the bands that mutate at the target sites. The targeted deep sequencing means that ligating the bands that cannot be digested with restriction endonuclease to the pMD19-T vector and then performing the deep sequencing, or directly ligating the PCR products to the pMD19-T vector and then performing the deep sequencing.

The four MsPALM1 allelic genes with simultaneous loss-of-function mutation means that none of the recovered DNA fragments comprising the target site can be digested with the restriction endonuclease, and the sequencing results show that four loss-of-function mutation sequences occurred at the target site of MsPALM1 gene, but there were no wild-type sequences occurred; or, the sequencing results of PCR products show that loss-of-function mutation occurred at the target site of all four MsPALM1 alleles, but there were no wild-type alleles occurred.

Wherein, the loss-of-function mutation means the occurrence of terminators or reading frame shifts at the target site of normal MsPALM1 coding sequences.

Further, the target site comprises one BstUI restriction endonuclease recognition site.

Further, the present disclosure also provides an application of artificial site-directed mutants of the compound leaf developmental regulatory gene MsPALM1 of *Medicago sativa* in *Medicago sativa* breeding and genome editing breeding.

The breeding method of the present disclosure can be used to produce multileaflet *Medicago sativa* varieties quickly in a short time period, with significant effects.

In particular, compared with traditional breeding methods, the present method has the following benefits:

① Short breeding period, the whole directional production process of the materials can be completed within 7 months, while the traditional hybridization method requires at least 3 to 5 years.

② Only one gene in the recipient varieties is changed, the obtained materials are changed to pentatrinate compound leaves with other agronomic trait unchanged; while the traditional hybridization method may introduce other genes linked with MsPALM1, which may influence the agronomic trait of the recipient varieties.

③ In strictly cross-pollinated autotetraploid *Medicago sativa*, a stable genetic homozygous mutant with all the four alleles mutated can be quickly obtained; However, it is very difficult to obtain a stable genetic homozygous mutant by the traditional hybridization method.

DETAILED DESCRIPTION

Figure 1:
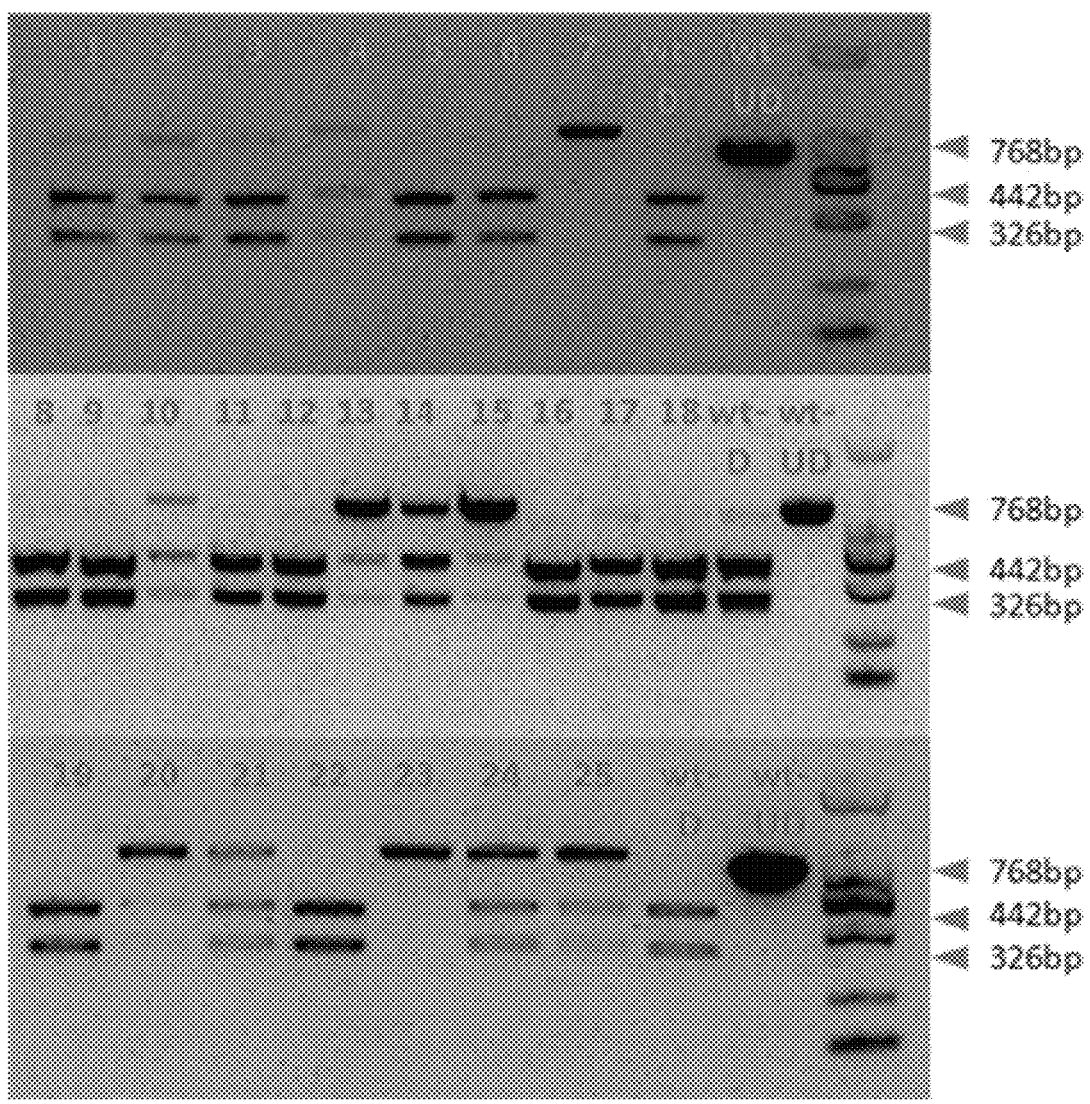
FIG. 1 shows the agarose gel electrophoresis results of PCR-RE analyses for screening PALM1 mutants out from the regenerated plants that are generated by transforming *Medicago sativa* with the CRISPR/Cas9 expression vector MsCRISPR/Cas9::PALM1 containing the guide sequence of the target site of PALM1 gene using *Agrobacterium tumefaciens*.

The test methods used in the following examples are all conventional methods, unless otherwise specifically noted.

The materials and reagents used in the following examples are all commercially available, unless otherwise specifically noted.

The breeding method employed in one example of the present disclosure will be described below.

First. Preparation of a recombinant vector for editing the *Medicago sativa* MsPALM1 gene 1.1. Selecting the reverse complementary sequence, 5′-GGAGACGAGCACGGTCGCGG-3′ (Seq ID NO. 3), of the nucleotide sequence 5′-CCGCGACCGTGCTCGTCTCC-3′ (Seq ID NO. 4) at the positions 323-343 after the translation initiation codon ATG in the single exon of MsPALM1 gene (HM038483) of *Medicago sativa* as the target site, and after the sequence was a PAM sequence "CGG". The sequence comprised one BstUI restriction endonuclease recognition site.

1.2. Synthesizing a forward oligonucleotide strand (MsPA1_1F) and a complementary reverse oligonucleotide strand (MsPA1_1R) according to the selected target site (BGI), The specific sequences were:

MsPA1_1F:
(Seq ID NO. 5)
<u>TTT</u>GGAGACGAGCACGGTCGCGG

MsPA1_1R:
(Seq ID NO. 6)
<u>AAAC</u>CCGCGACCGTGCTCGTCTC

Wherein, the non-underlined parts were the sequence from the target site or its complementary sequence without NGG, and the underlined parts were the cohesive ends for ligating the vector.

1.3. After annealing, the two strands MsPA1_1F and MsPA1_1R were annealed to form a double-stranded DNA with cohesive ends, which was used as the insertion fragment for constructing the recombinant vector.

1.4. Digesting the *Medicago sativa* CRISPR/Cas9 binary expression vector MsCRISPR/Cas9 comprising an sgRNA expression frame (its nucleotide sequence was as shown in Seq ID NO. 1) that can be expressed in *Medicago sativa* cells and a Cas9 gene expression frame (its nucleotide sequence was as shown in Seq ID NO. 2) that can be expressed in *Medicago sativa* cells with AarI endonuclease (NEB Co.) at 37° C.; cutting the *Medicago sativa* CRISPR/Cas9 expression vector with AarI endonuclease for 8 hours; inactivating the digestion system at 65° C. for 10 minutes, as the backbone fragments for constructing the recombinant vector.

1.5. Ligating the MsCRISPR/Cas9 vector backbone fragments and the insertion fragments with T4 DNA ligase (NEB Co.) to construct a vector MsCRISPR/Cas9::PALM1 for MsPALM1 editing, and then transferring into the *Escherichia coli*. After verification by sequencing, the positive transformants were extracted to form a recombinant vector MsCRISPR/Cas9::PALM1 for genome editing of *Medicago sativa* MsPALM1 gene.

Second. Genome editing of *Medicago sativa* MsPALM1 gene editing by stably transformation with *Agrobacterium* and acquisition of multileaflet *Medicago sativa* materials.

2.1. The obtained recombinant vector MsCRISPR/Cas9::PALM1 for genome editing of *Medicago sativa* MsPALM1 gene was transformed into *Agrobacterium tumefaciens* EHA105 (preserved by Guangdong Sanjie Forage Biotech Co., Ltd.) by a freezing-thawing method, to obtain positive clones.

2.2. Taking mature seeds of *Medicago sativa* varieties, they were washed with sterile water for 5 times, and soaked with 75% alcohol for 1 min. After discarding the alcohol, the seeds were washed with sterile water for 5 times, soaked with 0.1% mercuric chloride solution for 20 min, and washed with sterile water for 5 times. The seeds were inoculated on the germinating medium and cultured in light at 26-28° C. for 7 days. When two cotyledons were just opened, the cotyledons and hypocotyls were cut for *Agrobacterium* transformation.

2.3. The *Agrobacterium tumefaciens* into which the recombinant expression vector was transferred was subjected to the genetic transformation of *Medicago sativa*, the specific transformation operations were as below:

1. Germination of *Medicago sativa* seeds: Plump and well-colored *Medicago sativa* seeds were selected, soaked with 75% alcohol for 2 minutes, washed with sterile water for two times, 1 minute for each time; then soaked with 0.1% mercuric chloride and shaken by hands for 10 minutes, and washed with sterile water for five times. The sterilized seeds were spread out in a large sterile culture dish containing filter papers, air-dried, inoculated on a MS solid medium, and germinated in an illuminated incubator or culture room for 7-14 days;

2. Induction of callus: Cotyledons and hypocotyls of the germinated seedlings were cut into small pieces with a sterile scalpel and inoculated in a callus induction medium, and cultured in an incubator or culture room in dark at 25±1° C. for 3 days. The ingredients of the callus induction medium were: SH basal medium+2 mg/L 2,4-D+0.2 mg/L KT+0.3 mg/L casein hydrolysate+30 g/L sucrose+8 g/L agar;

3. Infection: 1-2 days in advance, the prepared *Agrobacterium tumefaciens* strains were inoculated in 50-100 mL YM liquid medium and cultured at 28° C. on a shaker at 200 r/min until the OD value 260/280 was between 0.5-0.8; the bacteria solution was transferred into a 50 mL sterile centrifuge tube, and centrifuged at 4° C. in a centrifuge at 4000 r/min for 12 minutes; the centrifuge tube was taken out, the supernatant was discarded, and a resuspension solution was added for resuspension until the OD value 260/280 was between 0.5-0.8; Corresponding volume of acetosyringone at 100 μmol/mL was added according to adding 100 μmol acetosyringone per liter, and the resuspension solution was MS liquid medium (MS+30 g/L sucrose); The explants induced in step 2 were collected into a 100 mL sterile triangular flask with a breathable and plastic sealing membrane, into which was poured a suitable amount of the resuspended bacteria solution (as long as covering the materials); The triangular flask was sealed with its own sealing membrane, and evacuated in a vacuum pump to 0.5 kpa for totally 1 h, during which the flask was shaken gently every 15 min; The triangular flask was taken out and shaken at 28° C. on a shaker at 120 r/m in for 1 h; All the bacteria solution was poured out, and the materials were spread out in a sterile culture dish containing filter papers to dry out;

4. Co-cultivation: The dried infected materials were inoculated in a co-cultivation medium (spreading a piece of sterile filter paper in the medium); the ingredients of the co-cultivation medium were: MS basal medium+2 mg/L 2,4-D+0.2 mg/L KT+30 g/L sucrose+8 g/L agar+100 μmol/L acetosyringone. They were cultivated in dark in an incubator or in a culture room at 25±1° C. for 3 days.

5. Screening: The co-cultivated materials were inoculated in a screening medium; the ingredients of the screening medium were: SH basal medium+2 mg/L 2,4-D+0.2 mg/L KT+30 g/L sucrose+8 g/L agar+250 mg/L cefotaxime+250 mg/L carbenicillin+15 mg/L hygromycin; they were cultivated in light in an incubator or in a culture room at 25±1° C. for 30-60 days;

6. Differentiation: The recovered materials were transferred into a differentiation medium; the ingredients of the differentiation medium were: UM basal medium+2 g/L casein hydrolysate+0.4 mg/L KT+30 g/L sucrose+8 g/L agar+250 mg/L cefotaxime+5 mg/L hygromycin; they were cultivated in light in an incubator or in a culture room at 25±1° C. for 15-30 days;

7. Rooting: The differentiated sprouts of 1-3 cm were transferred into a rooting medium; the ingredients of the rooting medium were: MS basal medium+1 mg/L IBA+15 g/L sucrose+8 g/L agar+250 mg/L cefotaxime.

25 regenerated *Medicago sativa* plants were obtained totally.

2.4. The genome DNA was extracted from the obtained 25 transgene *Medicago sativa* plants containing the recombinant vector targeting the *Medicago sativa* MsPALM1 gene by means of a plant genome extraction mini kit (Tiangen Biotech Co., Ltd). With the genome DNA as the template, the sequence containing a target site was subjected to PCR amplification by using an ExTaq DNA polymerase (Takara Co.), wherein the primers used for PCR amplification were:

```
MsPA1 genome F:
                                        (Seq ID NO. 7)
AATTTCATCCCCCACCCCATTA MsPA1 genome R:
                                        (Seq ID NO. 8)
TTCTCCACACACTGAAAAAGAGAGA
```

2.5 The obtained PCR amplification fragments were digested with BstUI restriction endonuclease (NEB Co.) to screen the mutants. The digestion results showed that, in the 25 tested plants, 13 plants contained mutations in the MsPALM1 gene, with a mutation efficiency of 52%, the results were as shown in FIG. 1; wherein there were 3 plants which were regenerated lines carrying four mutated MsPALM1 alleles, with a mutation efficiency of 12%.

Figures 2, 3:
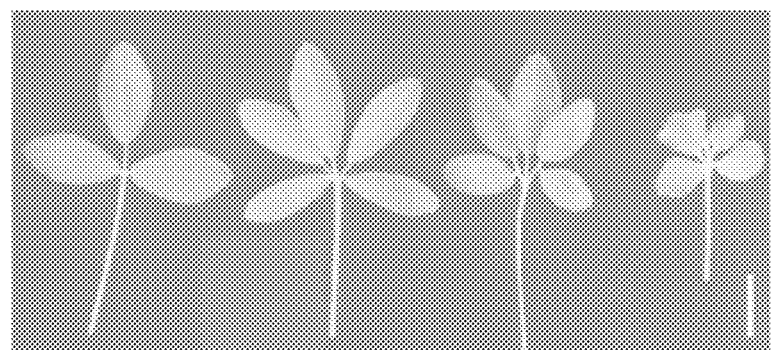
FIG. 2 shows the partial sequencing results of PCR products of PALM1 gene of *Medicago sativa* wild-type and mutant-type plants, where line 1 (WT) is Seq ID NO. 9, line 2 (−1) is Seq ID NO. 10, line 3 (−4) is Seq ID NO. 11, line 4 (−4) is Seq ID NO. 12, line 5 (+1) is Seq ID NO. 13, line 6 (−60) is Seq ID NO. 14, and line 7 (−11/+2) is Seq ID NO. 15.
FIG. 3 shows the leaf phenotype of wild-type and mutant-type plants obtained by transforming *Medicago sativa* with the CRISPR/Cas9 expression vector containing the guide sequence of the target site of PALM1 gene using *Agrobacterium tumefaciens*.

2.6. Bands which cannot be digested with BstUI restriction endonuclease were cloned by TA to ligate with the pMD19-T vector (Takara Co) and transformed into *Escherichia coli* DH5a (preserved by Guangdong Sanjie Forage Biotech Co., Ltd.); 10 monoclones were selected and sequenced by using M13F universal primers, and the mutations at the target sites were analyzed. The sequencing results showed that, there were mutations at the target sites in all the mutated plants obtained from the screening. Partial results were as shown in FIG. 2 (The shaded part of the image, that was, CCGCGACCGTGCTCGTCTCC starting from position 10 was the target site for editing), the forms of mutation included the insertion and/or deletion of bases.

2.7. The compound leaf phenotypes of the regenerated plants carrying four MsPALM1 allelic genes with simultaneous loss-of-function mutation were observed, wherein the compound leaves of 3 *Medicago sativa* plants showed pentatrinate compound leaves phenotypes significantly, indicating that the 3 transgene lines carrying four MsPALM1 allelic genes with simultaneous loss-of-function mutation were the directed produced multileaflet *Medicago sativa* materials, see FIG. 3.

Compared with traditional breeding methods, the present method has the following benefits:

① Short breeding period, the whole directional production process of the materials can be completed within 7 months, while the traditional hybridization method requires at least 3 to 5 years.

② Only one gene in the recipient varieties is changed, the obtained materials are changed to pentatrinate compound leaves with other agronomic trait unchanged; while the traditional hybridization method may introduce other genes linked with MsPALM1, which may influence the agronomic trait of the recipient varieties.

③ In strictly cross-pollinated autotetraploid *Medicago sativa*, a stable genetic homozygous mutant with all the four alleles mutated can be quickly obtained; However, it is very difficult to obtain a stable genetic homozygous mutant by the traditional hybridization method.

What is claimed is:

1. A method of obtaining multileaflet *Medicago sativa* materials comprising loss-of-function MsPALM1 alleles, the method comprising:
   Step (1), Introducing into a *Medicago sativa* cell an sgRNA which targets a sequence in the MsPALM1 gene and an expression cassette encoding a Cas9 protein wherein the sgRNA comprises the sequence set forth in SEQ ID NO:4;
   Step (2), Cutting the target site in the MsPALM1 gene;
   Step (3), Regenerating plants from the *Medicago sativa* cells in step 2
   Step (4), Screening the regenerated plants for the presence of loss-of-function MsPALM1 alleles;
   Step (5), Selecting the regenerated plants carrying four loss-of-function alleles for phenotypic identification, observing the compound leaf phenotype of the regenerated plants, and selecting plants with more than 3 leaflets in all the compound leaves as the generated multileaflet *Medicago sativa* materials.

2. The method of claim 1, wherein the sgRNA is introduced via an expression cassette comprising the MtU6 promoter.

3. The method of claim 1, wherein expression cassette encoding the Cas9 protein is operably linked to a CaMV 35S promoter and a tNOS terminator.

4. The method of claim 1, wherein screening of step 4 comprises PCR amplification of the MsPALM1 gene region corresponding to the target site and restriction endonuclease digestion of the PCR products.

5. The method of claim 1, wherein screening of step 4 comprises deep sequencing of the MsPALM1 gene region corresponding to the target site.

6. The method of claim 1, further comprising using the multileaflet *Medicago sativa* plant produced by the method in conventional plant breeding methods.

* * * * *

SEQUENCE LISTING

<160> NUMBER OF SEQ ID NOS: 2

<210> SEQ ID NO 1
<211> LENGTH: 615
<212> TYPE: DNA
<213> ORGANISM: artificial sequence
<220> FEATURE:
<223> OTHER INFORMATION: sgRNA expression cassette

<400> SEQUENCE: 1

```
atccaacatt tcacttgagt taactcaata gcaagaataa cgtccatagt ttcagcattc      60
aagcaaaacg gccaagaaaa tcagcttggt aatttcagtg agacctggac taccataagc     120
agcaccgcct attacactta atggggtaaa gtaaaacgag ccacatcacc tccttgattt     180
taaggagcat ttgaaggagt ataaaaagaa tgtatgtaat gtaaggttgt gttgtgtcat     240
tcaagatagc aagacggacc aaagcttcta tgtatctatc tatgtctatg atatgatgat     300
tgtattgatt tggtttgagt acagtgaggg agagggagga acttcttcac ttgtttattt     360
aacctgaaac tcaactcaaa tcactgagag tgaatgttga gaataagta ttatgttatg      420 tttgctttgc tattagtccc acatcgctta catatacttc agttatattg tttatatagc     480
ctagacgaac agcagggttt ggctcgcagg tgaacacaac acctgcacac gttttagagc     540
tagaaatagc aagttaaaat aaggctagtc cgttatcaac ttgaaaaagt ggcaccgagt     600
cggtgctttt ttttt                                                     615
```

<210> SEQ ID NO 2
<211> LENGTH: 5048
<212> TYPE: DNA
<213> ORGANISM: artificial sequence
<220> FEATURE:
<223> OTHER INFORMATION: Cas9 nuclease expression cassette

<400> SEQUENCE: 2

```
tgagactttt caacaaaggg tgatatccgg aaacctcctc ggattccatt gcccagctat      60
ctgtcacttt attgtgaaga tagtggaaaa ggaaggtggc tcctacaaat gccatcattg     120
cgataaagga aaggccatcg ttgaagatgc ctctgccgac agtggtccca agatggacc      180 cccacccacg aggagcatcg tggaaaaaga agacgttcca accacgtctt caaagcaagt     240
ggattgatgt gatatctcca ctgacgtaag ggatgacgca caatcccact atccttcgca     300
agacccttcc tctatataag gaagttcatt tcatttggag aggacctcga cctcaacaca     360
acatatacaa aacaaacgaa tctcaagcaa tcaagcattc tacttctatt gcagcaatt       420 aaatcatttc ttttaaagca aaagcaattt tctgaaaatt ttcaccattt acgaacgata     480
ctcgagatgg actataagga ccacgacgga gactacaagg atcatgatat tgattacaaa     540
gacgatgacg ataagatggc cccaaagaag aagcggaagg tcggtatcca cggagtccca     600
gcagccgaca agaagtacag catcggcctg gacatcggca ccaactctgt gggctgggcc     660
gtgatcaccg acgagtacaa ggtgccagc aagaaattca aggtgctggg caacaccgac      720
cggcacagca tcaagaagaa cctgatcgga gccctgctgt tcgacagcgg cgaaacagcc     780
gaggccaccc ggctgaagag aaccgccaga agaagataca ccagacgaaa gaaccggatc     840
tgctatctgc aagagatctt cagcaacgag atggccaagg tggacgacag cttcttccac     900
agactggaag agtccttcct ggtggaagag gataagaagc acgagcggca ccccatcttc     960
ggcaacatcg tggacgaggt ggcctaccac gagaagtacc ccaccatcta ccacctgaga    1020
aagaaactgg tggacagcac cgacaaggcc gacctgcggc tgatctatct ggccctggcc    1080
cacatgatca gttccggggg ccacttcctg atcgagggcg acctgaaccc cgacaacagc    1140
gacgtggaca gctgttcat ccagctggtg cagacctaca accagctgtt cgaggaaaac     1200
cccatcaacg ccagcggcgt ggacgccaag gccatcctgt ctgccagact gagcaagagc    1260
agacggctgg aaaatctgat cgcccagctg cccggcgaga gaagaatgg cctgttcgga     1320 aacctgattg ccctgagcct gggcctgacc cccaacttca gagcaacttt cgacctggcc    1380
```

```
gaggatgcca aactgcagct gagcaaggac acctacgacg acgacctgga caacctgctg    1440
gcccagatcg gcgaccagta cgccgacctg tttctggccg ccaagaacct gtccgacgcc    1500
atcctgctga gcgacatcct gagagtgaac accgagatca ccaaggcccc cctgagcgcc    1560
tctatgatca gagatacga cgagcaccac caggacctga ccctgctgaa agctctcgtg    1620
cggcagcagc tgcctgagaa gtacaaagag attttcttcg accagagcaa gaacggctac    1680
gccggctaca ttgacggcgg agccagccag gaagagttct acaagttcat caagcccatc    1740
ctggaaaaga tggacggcac cgaggaactg ctcgtgaagc tgaacagaga ggacctgctg    1800
cggaagcagc ggaccttcga caacggcagc atcccccacc agatccacct gggagagctg    1860
cacgccattc tgcggcggca ggaagatttt tacccattcc tgaaggacaa ccgggaaaag    1920
atcgagaaga tcctgacctt ccgcatcccc tactacgtgg ccctctggc cagggg aaac    1980 agcagattcg cctggatgac agaaagagc gaggaaacca tcaccccctg gaacttcgag    2040
gaagtggtgg acaagggcgc ttccgcccag agcttcatcg agcggatgac caacttcgat    2100
aagaacctgc ccaacgagaa ggtgctgccc aagcacagcc tgctgtacga gtacttcacc    2160
gtgtataacg agctgaccaa agtgaaatac gtgaccgagg aatgagaaa gcccgccttc    2220 ctgagcggcg agcagaaaaa ggccatcgtg acctgctgt tcaagaccaa ccggaaagtg    2280
accgtgaagc agctgaaaga ggactacttc aagaaaatcg agtgcttcga ctccgtggaa    2340
atctccggcg tggaagatcg gttcaacgcc tccctgggca cataccacga tctgctgaaa    2400
attatcaagg acaaggactt cctggacaat gaggaaaacg aggacattct ggaagatatc    2460
gtgctgaccc tgacactgtt tgaggacaga gagatgatcg aggaacggct gaaaacctat    2520 gcccaccctgt tcgacgacaa agtgatgaag cagctgaagc ggcggagata caccggctgg    2580
ggcaggctga gccggaagct gatcaacggc atccgggaca gcagtccgg caagacaatc    2640 ctggatttcc tgaagtccga cggcttcgcc aacagaaact tcatgcagct gatccacgac    2700
gacagcctga ccttaaaga ggacatccag aaagcccagg tgtccggcca gggcgatagc    2760
ctgcacgagc acattgccaa tctggccggc agccccgcca ttaagaaggg catcctgcag    2820
acagtgaagg tggtggacga gctcgtgaaa gtgatgggcc ggcacaagcc cgagaacatc    2880
gtgatcgaaa tggccagaga gaaccagacc acccagaagg gacagaagaa cagccgcgag    2940
agaatgaagc ggatcgaaga gggcatcaaa gagctgggca gccagatcct gaaagaacac    3000
cccgtggaaa acacccagct gcagaacgag aagctgtacc tgtactacct gcagaatggg    3060
cgggatatgt acgtggacca ggaactggac atcaaccggc tgtccgacta cgatgtggac    3120
catatcgtgc ctcagagctt tctgaaggac gactccatcg acaacaaggt gctgaccaga    3180
agcgacaaga accggggcaa gagcgacaac gtgcccctcg aagaggtcgt gaagaagatg    3240
aagaactact ggcggcagct gctgaacgcc aagctgatta cccagagaaa gttcgacaat    3300
ctgaccaagg ccgagagagg cggcctgagc gaactggata aggccggctt catcaagaga    3360
cagctggtgg aaacccggca gatcacaaag cacgtggcac agatcctgga ctcccggatg    3420
aacactaagt acgacgagaa tgacaagctg atccgggaag tgaaagtgat caccctgaag    3480
tccaagctgg tgtccgattt ccggaaggat ttcagttttt acaaagtgcg cgagatcaac    3540
aactaccacc acgcccacga cgcctacctg aacgccgtcg tgggaaccgc cctgatcaaa    3600
aagtacccta agctggaaag cgagttcgtg tacggcgact acaaggtgta cgacgtgcgg    3660
aagatgatcg ccaagagcga gcaggaaatc ggcaaggcta ccgccaagta cttcttctac    3720
```

```
-continued agcaacatca tgaactttt  caagaccgag attaccctgg ccaacggcga gatccggaag    3780
cggcctctga tcgagacaaa cggcgaaacc ggggagatcg tgtgggataa gggccgggat    3840
tttgccaccg tgcggaaagt gctgagcatg ccccaagtga atatcgtgaa aaagaccgag    3900
gtgcagacag gcggcttcag caaagagtct atcctgccca agaggaacag cgataagctg    3960
atcgccagaa agaaggactg ggaccctaag aagtacggcg gcttcgacag ccccaccgtg    4020
gcctattctg tgctggtggt ggccaaagtg gaaaagggca agtccaagaa actgaagagt    4080
gtgaaagagc tgctggggat caccatcatg gaaagaagca gcttcgagaa gaatcccatc    4140
gactttctgg aagccaaggg ctacaaagaa gtgaaaaagg acctgatcat caagctgcct    4200
aagtactccc tgttcgagct ggaaaacggc cggaagagaa tgctggcctc tgccggcgaa    4260
ctgcagaagg gaaacgaact ggccctgccc tccaaatatg tgaacttcct gtacctggcc    4320
agccactatg agaagctgaa gggctccccc gaggataatg agcagaaaca gctgtttgtg    4380
gaacagcaca agcactacct ggacgagatc atcgagcaga tcagcgagtt ctccaagaga    4440
gtgatcctgg ccgacgctaa tctggacaaa gtgctgtccg cctacaacaa gcaccgggat    4500
aagcccatca gagagcaggc cgagaatatc atccacctgt ttaccctgac caatctggga    4560
gcccctgccg ccttcaagta ctttgacacc accatcgacc ggaagaggta caccagcacc    4620
aaagaggtgc tggacgccac cctgatccac cagagcatca ccggcctgta cgagacacgg    4680
atcgacctgt ctcagctggg aggcgacaaa aggccggcgg ccacgaaaaa ggccggccag    4740
gcaaaaaaga aaaagtaagg atcctgattg atcgatagag ctcgaatttc cccgatcgtt    4800
caaacatttg gcaataaagt ttcttaagat tgaatcctgt tgccggtctt gcgatgatta    4860
tcatataatt tctgttgaat tacgttaagc atgtaataat taacatgtaa tgcatgacgt    4920
tatttatgag atgggttttt atgattagag tcccgcaatt atacatttaa tacgcgatag    4980
aaaacaaaat atagcgcgca aactaggata aattatcgcg cgcggtgtca tctatgttac    5040
tagatcgg                                                             5048
```